United States Patent [19]

Pearce

[11] Patent Number: 5,070,870
[45] Date of Patent: Dec. 10, 1991

[54] DISPENSERS FOR POWDERED MEDICATION

[76] Inventor: John O. Pearce, 33 St. Patrick's Road, Nuthall, Nottingham, NG 16 1ED, England, NG16 1ED

[21] Appl. No.: 571,592

[22] PCT Filed: Feb. 22, 1989

[86] PCT No.: PCT/GB89/00165
§ 371 Date: Aug. 22, 1990
§ 102(e) Date: Aug. 22, 1990

[87] PCT Pub. No.: WO89/07464
PCT Pub. Date: Aug. 24, 1989

[30] Foreign Application Priority Data

Feb. 22, 1988 [GB] United Kingdom ............... 8804069

[51] Int. Cl.⁵ ................. A61M 15/00; A61M 16/00; B05D 7/14; B65M 83/06
[52] U.S. Cl. ........................ 128/203.15; 128/203.12
[58] Field of Search ............... 128/203.12, 203.14, 128/203.15, 203.21

[56] References Cited

U.S. PATENT DOCUMENTS

| 2,517,482 | 8/1950 | Hall | 128/203.15 |
| 3,870,046 | 3/1975 | Elliott | 128/203.15 |
| 4,069,819 | 1/1978 | Valentini et al. | 128/203.15 |
| 4,860,740 | 8/1989 | Kirk et al. | 128/203.15 |

FOREIGN PATENT DOCUMENTS 0041783 12/1981 European Pat. Off.
0129985 1/1985 European Pat. Off.

Primary Examiner—Edgar S. Burr
Assistant Examiner—Lisa E. Malvaso
Attorney, Agent, or Firm—Armstrong, Nikaido, Marmelstein, Kubovcik & Murray

[57] ABSTRACT

A dispenser (10) for powdered medication comprising a housing (50) for piercing a capsule containing powdered medication, a generally cylindrical member (30) adapted to receive the capsule and in which the capsule can rotate freely to release the powdered medication, and a mouthpiece (20) through which the powdered medication can be drawn from the chamber (30), in which the chamber has three air inlets (37, 38, 39) spaced around the cylindricla wall of the chamber.

8 Claims, 3 Drawing Sheets

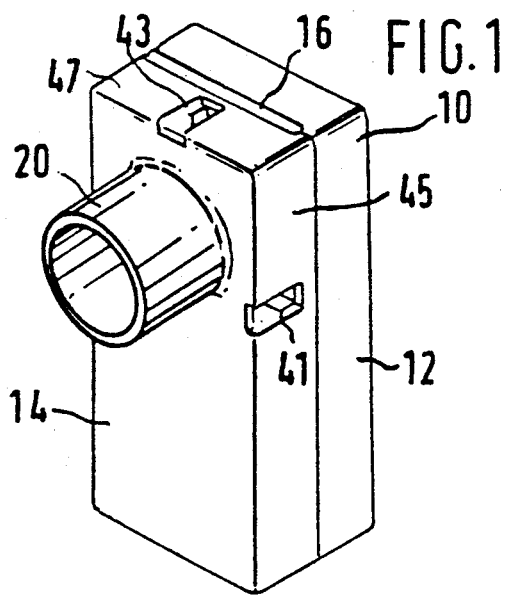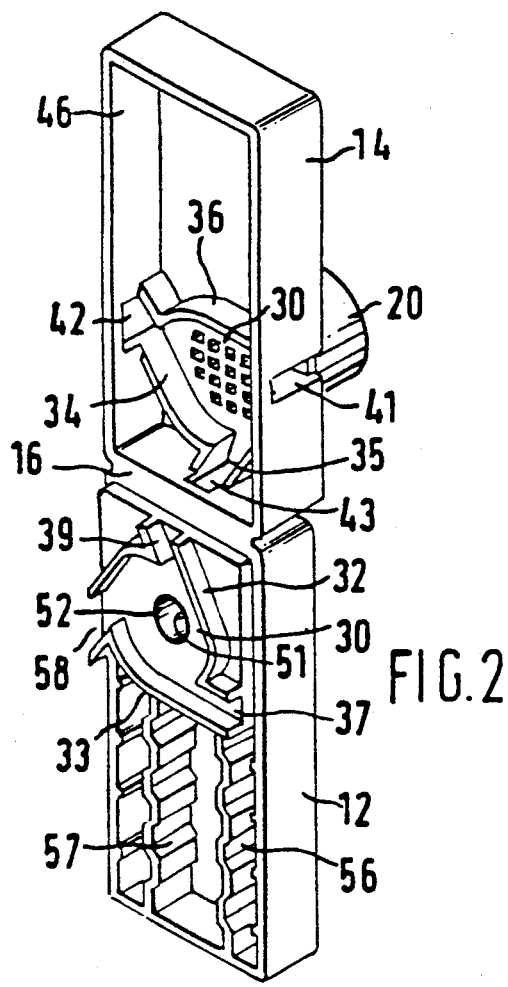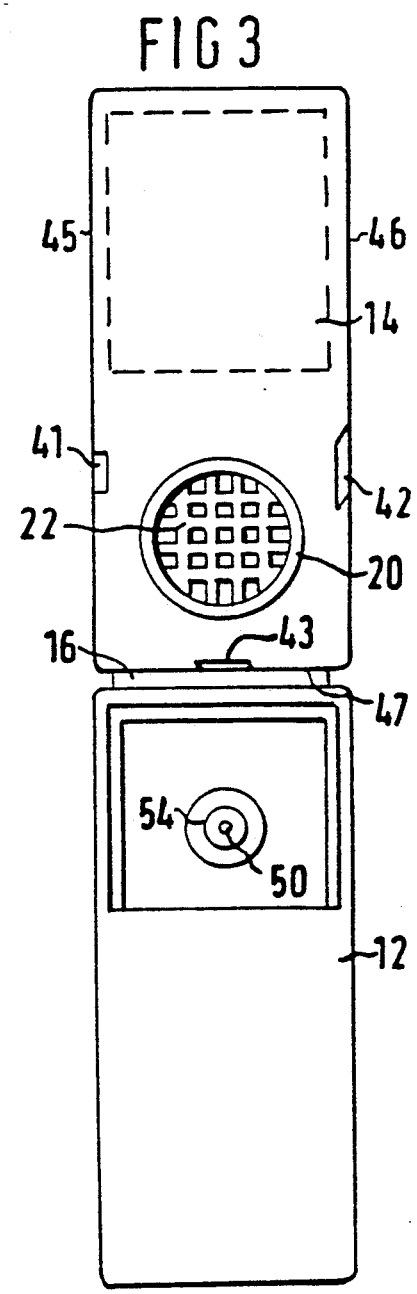

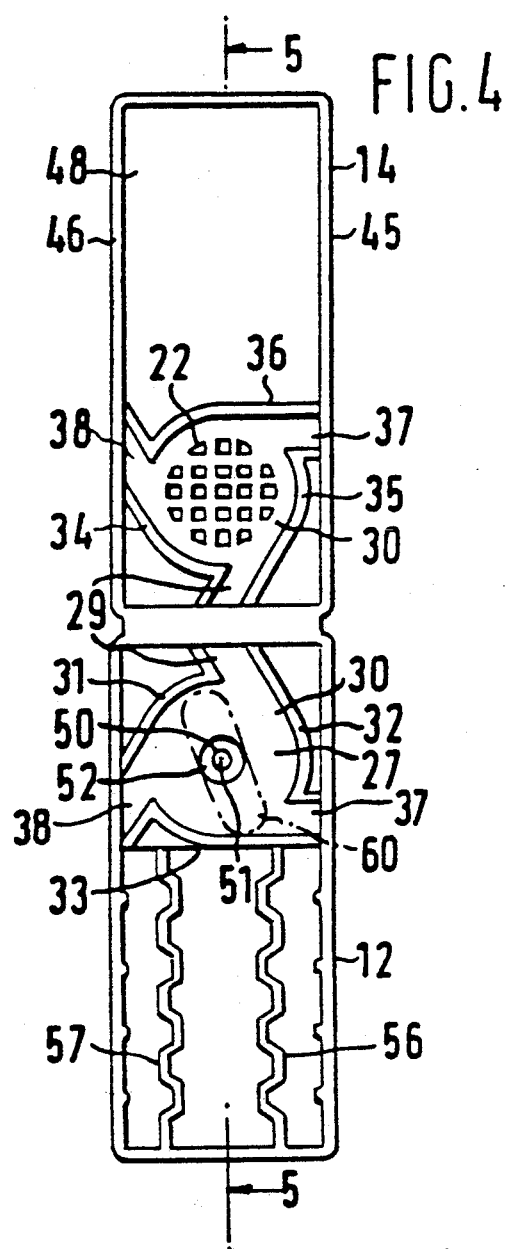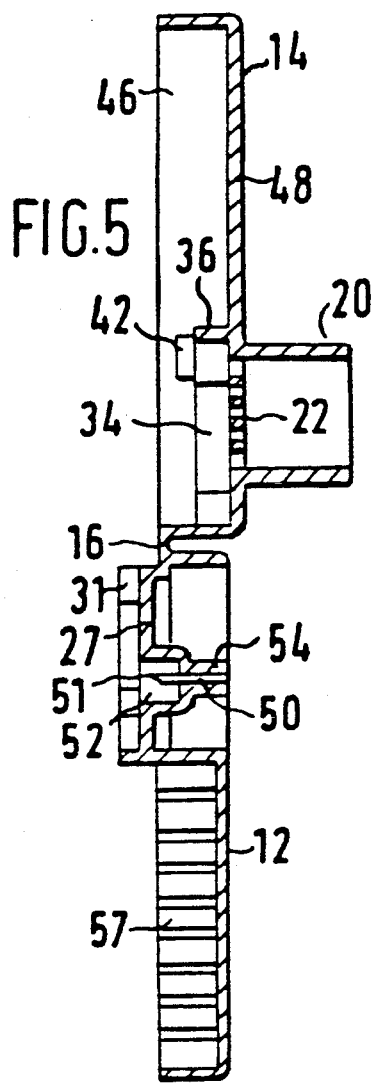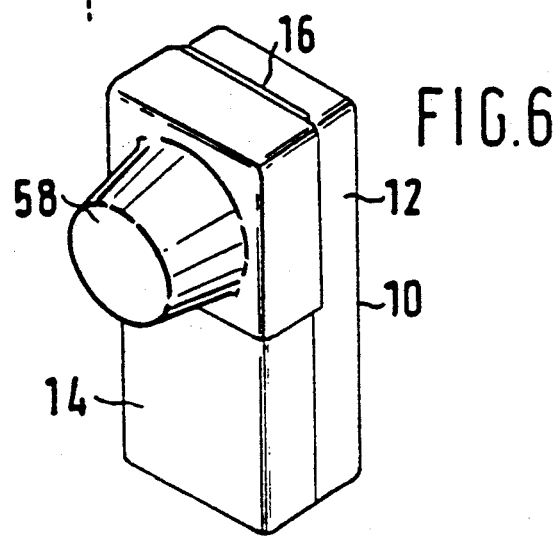

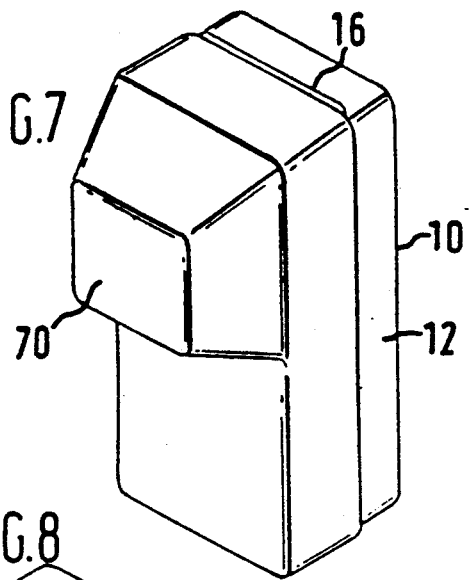
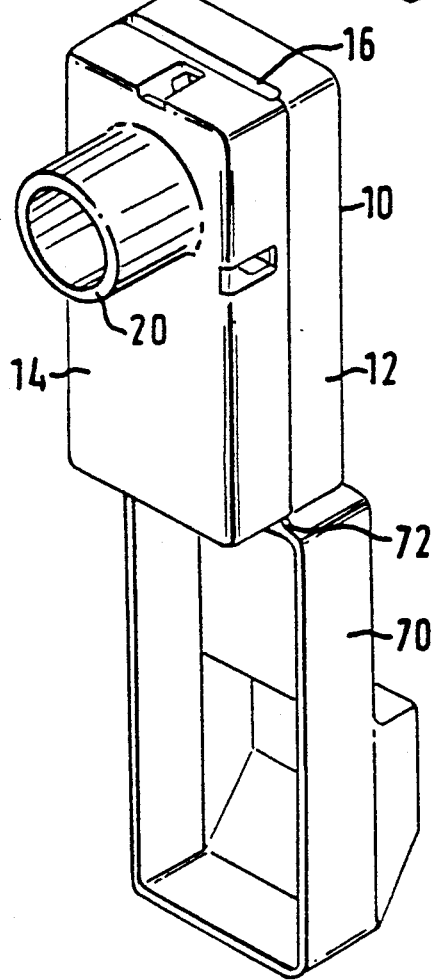
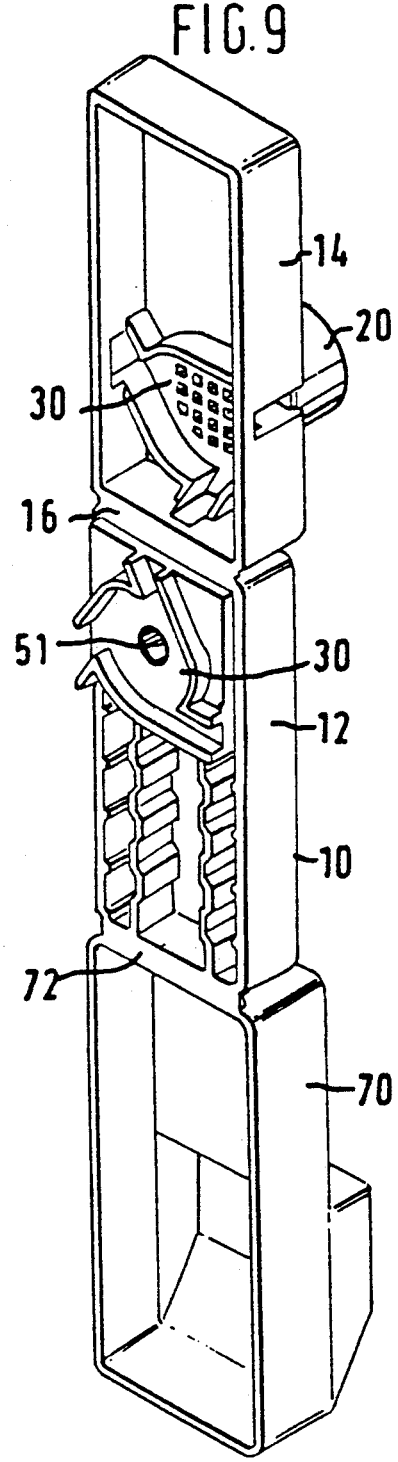

DISPENSERS FOR POWDERED MEDICATION

This invention relates to dispensers for powdered medication.

Medication in powder form for inhalation by the patient, for example, drugs for treatment of asthma, are supplied in capsules containing individual doses. Dispensers for such medication usually consist of a chamber which can receive a capsule and from which the powder can be inhaled through a mouthpiece, after the capsule has been broken or pierced.

This invention is concerned in particular with dispensers of the kind having means for piercing a capsule and a chamber shaped so that a pierced capsule in the chamber is rotated by the airflow through the chamber in use, so that powder is shaken from the capsule into the chamber.

There are a number of dispensers currently available, which have various disadvantages. In particular, there is a risk of the capsule becoming jammed in the chamber so that it does not rotate freely: this can be a problem particularly for asthmatics, who cannot generate the increased suction pressure necessary to start the capsule turning. Some of the dispensers have relatively complicated mechanisms for piercing the capsule and for ejecting empty capsules, which make the dispenser expensive to manufacture.

It is an object of this invention to provide a dispenser which is effective in operation but which can be manufactured relatively cheaply.

The present invention provides a dispenser for powdered medication comprising static means for piercing a capsule containing powdered medication, a chamber adapted to receive a pierced capsule and in which the capsule can rotate freely to release the powdered medication, and a mouthpiece through which the powdered medication can be drawn from the chamber, in which the dispenser comprises a body formed from the two parts hinged together for movement between a closed position and an open position characterised in that cooperating elements of the two parts form the chamber, the elements consisting of flanges which form part or all of the cylindrical walls of the chamber, the chamber having at least three inlets comprising passages which extend tangentially from the cylindrical walls, and in which the elements on one of the parts form an open receptacle in which a capsule can be deposited.

Preferably, the means for piercing the capsule comprise a piercing element located in the receptacle formed by the said elements. Suitably, the elements consist of flanges which, in the closed position, form part or all of the curved walls of the chamber, and which project from a flat surface forming one side wall of the chamber. The means for piercing the capsule may be fixed in a depression in the flat surface within the volume of the chamber.

The cooperating elements on the other part of the body may be correspondingly shaped flanges projecting from one wall of the body. The mouthpiece is preferably, a tubular element projecting from the wall on the opposite side to the flanges, the wall being pierced to provide communication between the chamber and the mouthpiece.

The two parts of the body may be formed from plastics, with an integral hinge.

Preferably, the two parts of the body define, in the closed position, a closed volume outside the chamber, which can be used to hold one or more capsules. The cooperating elements are preferably shaped to form a chamber having three inlets, the chamber having a cylindrical wall. The inlets preferably consist of inlet passages extending to openings in three faces of the body, which may be generally in the shape of a rectangular box.

Preferably the inlets are regularly spaced around the chamber. The inlets preferably comprise passages extending tangentially from the wall of the chamber.

A cover may be provided for the mouthpiece. In one form of the invention, the cover is hinged to one part of the body. The invention will now be described by way of example only, with reference to the accompanying drawings in which:

FIG. 1 is a perspective view of a dispenser for powdered medication in accordance with the invention, FIG. 2 is a perspective view of the dispenser in the opened position, FIG. 3 is a front view of the dispenser in the opened position, FIG. 4 is a rear view of the dispenser in the opened position.

FIG. 5 is a section on line 5—5 of FIG. 4,

FIG. 6 is a perspective view of the dispenser fitted with a mouthpiece cap, and

FIGS. 7, 8 and 9 are perspective views of a modified embodiment of the invention, provided with an integral mouthpiece cap. Referring to FIGS. 1 to 6, the dispenser is in the shape of a rectangular box which can be held in the hand, having a body 10 and a mouthpiece 20. Inside the body is formed a chamber 30 which can receive a capsule and from which powder can be drawn via the mouthpiece 20. The chamber 30 has three air inlets as described below, and is provided with a pin 50 with which a capsule can be pierced.

The body 10 has a rear part 12 and a front part 14, joined together by an integral hinge 16. Three flanges 31, 32, 33 on the rear part 12 engage, when the dispenser is closed, with corresponding flanges 34, 35, 36 on the front part 14 to form the cylindrical walls of the chamber 30. The flanges on the rear part project from a floor 27 spaced inwards from the rear wall 13 of the rear part 12, so that the internal front-to-rear dimension of the chamber 30 is slightly greater than the thickness of the largest capsules to be accommodated. As shown in FIGS. 2 and 4, the chamber 30 is essentially cylindrical, with three inlet passages 37, 38, 39 arranged at 120° intervals around the cylindrical wall of the chamber. Each inlet passage has one wall defined by a tangentially extending part of the cylindrical chamber wall. The inlet passages extend to openings 41, 42, 43 in the two side walls 45 and 46 and the upper wall 47 of the front part 14 of the dispenser. The inlet passages, which are square in cross-section, have dimensions slightly less than the thickness of the smallest capsule to be accommodated. This prevents the risk of a capsule entering one of the inlet passages, whilst providing the maximum cross-sectional area for the inlet passages, to give a large flow of air at relatively low suction pressure.

The mouthpiece 20 consists of a tube of suitable dimensions [typically 19 mm in diameter] projecting from the front wall 48 of the body 10 at a position overlying the chamber 30. The mouthpiece is separated from the chamber 30 by a grill 22 formed by perforations in the wall 48.

The floor 27 forming one wall of the chamber in the rear part 12, is shaped to form a centrally positioned recess 52 which can receive one end of a capsule. A boss 54 projecting rearwards from the recess has a bore in which is push-fitted a metal pin 50. The pointed end 51 of the pin projects into the recess 52, but lies below the level of the floor 27. The end 51 is shaped so as to form a suitably large aperture in a capsule which is pushed into the recess.

The chamber 30 and mouthpiece 20 are formed in the upper part of the body. The remainder of the body serves as a handle to enable the dispenser to be held comfortably during use, and additionally provides storage space for a small number of capsules. To this end, the rear part 12 is formed with two corrugated flanges 56 and 57 to enable the capsules to be held in place between the flanges and the sides of the body.

A suitable catch [not shown] can be provided to hold the two parts of the dispenser together in the closed position.

The dispenser [except for the pin 50] can be formed in one piece from a suitable plastic, such as polypropylene.

A detachable cover 58 [FIG. 6] can be provided for the mouthpiece 20.

In the use of the dispenser, the front and rear parts are released from one another and moved to the open position and the rear part 12 is held so that the floor 27 of the open chamber 30 is horizontal. A capsule is pushed end first into the recess 52 so that the pin 50 pierces the end of the capsule. The capsule is then pulled from the recess and placed in the chamber 30, for example as shown in broken lines at 60 in FIG. 4. The front part 14 is moved to the closed position and the dispenser turned upright to the position shown in FIG. 1. The user then places the mouthpiece 20 in his mouth and inhales to draw air through the inlets to the chamber 30 and out through the grill 22. Because of the arrangement of the inlet passages, the airflow through the chamber causes the capsule to rotate, so that the powder is shaken out through the pierced end of the capsule into the chamber 30, from where it is drawn through the grill 22 into the patient's air passages. It is believed that piercing one end of the capsule will be sufficient: however, in some cases it may be necessary, after piercing one end of the capsule, to turn it over and pierce the other end to ensure that all the powder is dispensed from the capsule. After use, the dispenser is opened and the empty capsule discarded.

Since the chamber 30 has three inlets, this ensures that whatever the position of the capsule in the chamber, at least one flow of air from one of the inlets will strike the capsule in such a position as to start it rotating. There is therefore less risk of the capsule being jammed in the chamber. By providing three air inlets with relatively large cross-sections, a sufficient flow of air through the chamber is provided even at relatively low pressure, which is advantageous, particularly when the dispenser is to be used, for example by people with asthma. It is found that increasing the cross-section of the inlet passages does not prevent the flow of air from producing a sufficiently rapid rotation of the capsule.

Since the dispenser can be formed by molding in one piece, and since it is not necessary to carry out the molding to close tolerances, the dispenser can be manufactured from inexpensive plastics, such as polypropylene.

The dimensions of the chamber 30 are such as to accommodate the required capsules. For example, in a dispenser designed for use with capsules of standard sizes "No. 2" and "No. 3", which have an overall length of approximately 18 mm, the curved parts of the walls of the chamber can be provided with an internal radius of curvature of 10 mm. The internal front-to-rear depth of the chamber is typically 8 mm, and the internal width of the inlet passages 4.5 mm.

FIGS. 7 to 9 illustrate a modified embodiment of the invention, which is provided with a cap 70 for the mouthpiece 20, the cap 70 being formed in one with the body 10 and connected to the rear part 12 of the body by an integral hinge 72.

It will be appreciated that other modifications could be made in the described embodiment. For example, although positioning the pin 50 in a recess in the floor of the chamber 30 has particular advantages, it would be possible to position the pin in other locations where it would not interfere with rotation of a capsule in the chamber, for example in one of the inlet passages.

I claim:

1. A dispenser for powdered medication comprising:
    a dispenser body (10) formed of two boxes open at one side and hinged together at an edge of the open side so as to form, respectively, a front part (14) and a rear part (12) of said body when said parts are pivoted to be juxtaposed in a closed position forming a closed volume within said body;
    a plurality of openings (41, 42, 43) formed, respectively, in each of a plurality of side surfaces of said body;
    a plurality of arcuately shaped flanges (34, 35, 36) formed within said body so as to form a wall of a generally cylindrical chamber (30) within said body, said flanges having terminal portions extended to inner side surfaces of said body adjacent said openings so as to form air passages (37, 38, 39) from said openings entering said chamber tangentially; and
    a mouthpiece (20) formed on a front wall (48) of said body (10) and communicating with said chamber (30),
    such that air drawn from said chamber through the mouthpiece will be replaced by air entering the chamber tangentially through said air passages, causing a rotary flow of air in said chamber to dispense medication from a pierced capsule, said capsule being freely held in said chamber so as to be rotatable about a transverse axis of the capsule by said air flow.

2. A dispenser as claimed in claim 1 further including means for piercing a capsule comprising a recess (52) formed in an inner surface of said body and a piercing element (50) located in the recess.

3. A dispenser as claimed in claim 1 or 2 wherein the two parts (12, 14) of the body are formed from plastics material with an integral hinge (16).

4. A dispenser as claimed in claim 1 or 2 wherein the two parts of the body (12, 14) define, in the closed position, a closed volume outside the chamber capable of being used to hold capsules.

5. A dispenser as claimed in claim 1 or 2 wherein the chamber has three air inlets (37, 38, 39) spaced around the chamber.

6. A dispenser as claimed in claim 5 wherein the inlets (37, 38, 39) are regularly spaced around the wall of the chamber.

7. A dispenser as claimed in claim 2 wherein said recess (52) and piercing element (50) are within a volume bounded by the chamber (30).

8. A dispenser as claimed in claim 1 wherein the mouthpiece (20) is a tubular element projecting from the front wall 48 of said body on a side opposite to the flanges, the wall being pierced to provide communication between the chamber (30) and the mouthpiece (20).

* * * * *